United States Patent

Lürssen

[11] 4,265,656
[45] May 5, 1981

[54] COMPOSITIONS AND METHODS FOR INHIBITING THE GROWTH OF CEREALS

[75] Inventor: Klaus Lürssen, Berg.-Gladbach, Fed. Rep. of Germany

[73] Assignee: Bayer Aktiengesellschaft, Leverkusen, Fed. Rep. of Germany

[21] Appl. No.: 74,593

[22] Filed: Sep. 11, 1979

[30] Foreign Application Priority Data

Sep. 28, 1978 [DE] Fed. Rep. of Germany ....... 2842220

[51] Int. Cl.³ .......................................... C07D 293/08
[52] U.S. Cl. ......................................... 71/103; 71/88; 71/90; 71/94; 544/59; 544/108; 546/184
[58] Field of Search ....................... 71/88, 90, 94, 103

[56] References Cited

U.S. PATENT DOCUMENTS

| | | | |
|---|---|---|---|
| 3,138,519 | 6/1964 | Riden, Jr. et al. | 71/103 |
| 3,856,501 | 12/1974 | Zeeh et al. | 71/90 |
| 3,905,798 | 9/1975 | Zeeh et al. | 71/76 |
| 3,963,479 | 6/1976 | Naumann et al. | 71/90 |
| 4,047,923 | 9/1977 | Naumann et al. | 71/90 |

FOREIGN PATENT DOCUMENTS 1550622 11/1968 France.
2342966 9/1977 France.

Primary Examiner—Donald G. Daus
Assistant Examiner—James H. Turnipseed
Attorney, Agent, or Firm—Sprung, Felfe, Horn, Lynch & Kramer

[57] ABSTRACT

A novel composition for inhibiting the growth of cereals comprising, as active ingredients,
(a) at least one haloethylsulfone of the formula

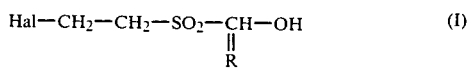

wherein Hal is halogen and
R is hydrogen or alkyl of 1 to 6 carbon atoms and
(b) at least one compound selected from
(i) (2-chloroethyl)-trimethylammonium compound of the formula

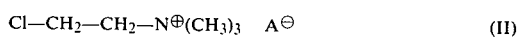 (II)

wherein
$A^{\ominus}$ is an equivalent of an anion of a non-phytotoxic acid,
(ii) ammonium compounds of the formula

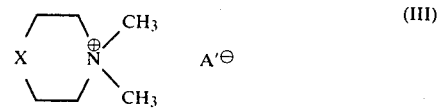 (III)

wherein
X is —CH$_2$—, oxygen, sulfur or the grouping $S^{\oplus}$—CH$_3$ $A''^{\ominus}$, and $A'^{\ominus}$ is an equivalent of an anion of a non-phytotoxic acid, and
(iii) sulfonium compound of the formula

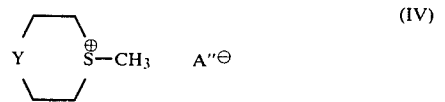 (IV)

wherein
Y is oxygen, sulfur or the grouping $S^{\oplus}$—CH$_2$ $A''^{\ominus}$, and $A''^{\ominus}$ is an equivalent of an anion of a non-phytotoxic acid.

15 Claims, No Drawings

COMPOSITIONS AND METHODS FOR INHIBITING THE GROWTH OF CEREALS

This invention relates to compositions and methods for inhibiting the growth of cereals. More specifically, the invention relates to synergistic combinations of haloethylsulfones and ammonium or sulfonium compounds, for inhibiting cereal growth.

It is known that certain haloethylsulfones, for example 2-chloroethyl hydroxymethylsulfone, can be used for inhibiting the growth of cereals (see DE-OS (German Published Specification) No. 2,675,380). However, the activity of these substances is not satisfactory, especially when low amounts are used.

Furthermore, it is already known that certain ammonium compounds and sulfonium compounds are capable of inhibiting the longitudinal growth of the stalks of cereals (see U.S. Pat. No. 3,156,554; U.S. Pat. No. 3,905,789; U.S. Pat. No. 3,542,538; DE-OS (German Published Specification) No. 2,217,697 and DE-OS (German Published Specification) No. 2,331,185). Nevertheless, in some cases, especially when low amounts are used, the activity of these products also leaves something to be desired.

The present invention now provides a cereal-growth inhibiting composition containing, as active ingredients,
(a) at least one haloethylsulfones of the formula $$Hal-CH_2-CH_2-SO_2-\underset{R}{\underset{\|}{CH}}-OH \qquad (I)$$

wherein
Hal is halogen and
R is hydrogen or alkyl with 1 to 6 carbon atoms, and
(b) at least one compound selected from (2-chloroethyl)trimethylammonium compound of the formula $$Cl-CH_2-CH_2-N^\oplus(CH_3)_3 \quad A^\ominus \qquad (II)$$

in which
$A^\ominus$ represents an equivalent of an anion of a non-phytotoxic acid,
ammonium compounds of the general formula

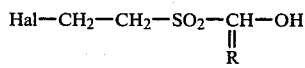

in which
X represents $-CH_2-$, oxygen, sulphur or the grouping $$S^\oplus-CH_3 A'^\ominus$$

and $A'^\ominus$ represents an equivalent of an anion of a non-phytotoxic acid, and
sulphonium compounds of the general formula

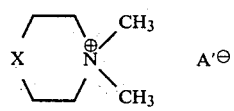

in which
Y represents oxygen, sulphur or the grouping $$S^\oplus-CH_3 A''^\ominus$$

and $A''^\ominus$ represents an equivalent of an anion of a non-phytotoxic acid,
alone or in admixture with a diluent or carrier.

Surprisingly, the growth-inhibiting action of the active compound combinations according to the invention on cereals is considerably higher than the sum of the actions of the individual active compounds. There is thus a true synergistic effect, which could not be foreseen, and not just a supplementary action. The active compound combinations according to this invention therefore represent a valuable enrichment of the art.

The formula (I) provides a general definition of the haloethyl sulfones contained in the active compound combinations according to the invention. In this formula, Hal preferably represents chlorine or bromine and R preferably represents hydrogen or straight-chain or branched alkyl with 1 to 4 carbon atoms, especially methyl, ethyl, n-propyl or iso-propyl.

Specific examples of haloethyl sulfones of the formula (I) are: 2-chloroethyl hydroxymethyl sulfone, 2-bromoethyl hydroxymethyl sulfone, 2-chloroethyl 1-hydroxyethyl sulfone, 2-bromoethyl 1-hydroxyethyl sulfone, 2-chloroethyl 1-hydroxy-n-propyl sulfone, 2-bromoethyl 1-hydroxy-n-propyl sulfone, 2-chloroethyl 1-hydroxy-n-butyl sulfone, 2-bromoethyl 1-hydroxy-n-butyl sulfone, 2-chloroethyl 1-hydroxy-iso-butyl sulfone and 2-bromoethyl 1-hydroxy-iso-butyl sulfone.

The haloethyl sulfones of the formula (I) are already known (see DE-OS (German Published Specification) No. 2,657,380).

The formula (II) provides a definition of the (2-chloroethyl)-trimethylammonium compounds which the active compound combinations according to the invention can contain. In this formula, $A^\ominus$ preferably represents chloride or bromide. Specific examples of compounds of the formula (II) which may be mentioned are: (2-chloroethyl)trimethylammonium chloride and (2-chloroethyl)-trimethylammonium bromide.

The (2-chloroethyl)-trimethylammonium compounds of the formula (II) are known (see U.S. Pat. No. 3,156,554).

The formula (III) provides a definition of the other ammonium compounds which the active compound combinations according to the invention can contain. In this formula, $A'^\ominus$ preferably represents halide (especially chloride, bromide or iodide), tetrafluoborate or alkyl-sulphate (especially methyl-sulphate or ethylsulphate).

Specific examples of compounds of the formula (III) are: 1,1-dimethyl-piperidinium chloride, 1,1-dimethyl-piperidinium bromide, 1,1-dimethyl-morpholinium chloride, 1,1-dimethyl-morpholinium bromide, 1,1-dimethyl-thiamorpholinium chloride, 1,1-dimethyl-thiamorpholinium bromide, 1-methylsulphonia-4-dimethyl-ammonia-cyclohexane dichloride and 1-methylsulphonia-4-dimethyl-ammonia-cyclohexane dimethosulphate.

The ammonium compounds of the formula (III) are known (see U.S. Pat. No. 3,905,798, U.S. Pat. No. 3,542,538, DE-OS (German Published Specification) No. 2,331,185, DE-OS (German Published Specification) No. 2,207,575 and DE-AS (German Published Specification) No. 1,642,215).

The formula (IV) provides a definition of the sulphonium compounds which the active compound combinations according to the invention can contain. In this formula, A″⊖ preferably represents halide (especially chloride, bromide or iodide), tetrafluoborate or alkyl-sulphate (especially methyl-sulphate or ethyl-sulphate).

Specific examples of compounds of the formula (IV) which may be mentioned are: 1-methylsulphonia-4-oxa-cyclohexane bromide, 1-methylsulphonia-4-oxa-cyclohexane chloride, 1-methylsulphonia-4-oxa-cyclohexane iodide, 1-methylsulphonia-4-thia-cyclohexane chloride, 1-methylsulphonia-4-thia-cyclohexane bromide, 1-methylsulphonia-4-thia-cyclohexane iodide, 1,4-dimethyl-1,4-disulphonia-cyclohexane dichloride and 1,4-dimethyl-1,4-disulphonia-cyclohexane dimethosulphate.

The sulphonium compounds of the formula (IV) are known (see DE-OS (German Published Specification) No. 2,217,697 and DE-OS (German Published Specification) No. 2,331,185).

The synergistic effect is particularly pronounced when the active compounds are present in the active compound combinations according to the invention in certain proportions. However, the weight ratios of the active compounds in the active compound combinations can vary within relatively wide limits. In general, 0.04 to 2 parts by weight, preferably 0.07 to 0.5 part by weight, of component (b), that is one or more active compounds of the formulae (II), (III) and (IV), are present per part by weight of component (a), that is one or more active compounds of the formula (I).

The active compound combinations according to the invention exhibit a powerful growth-inhibiting activity in cereals. This is of importance because lodging of the stalks of the cereal is thereby largely avoided, even under unfavorable weather conditions. By using the active compound combinations according to the invention it is furthermore possible to apply a fertilizer containing larger than usual amounts of nitrogen fertilizer without the danger of the cereal lodging. Increased yields can thus be achieved by use of the active compound combinations according to the invention in association with the application of a larger amount of fertilizer.

By cereals in the present case there are to be understood all the customary varieties of cereal, preferably oats, rye, barley, wheat and rice.

The active compounds can be converted into the customary formulations, such as solutions, emulsions, suspensions, powders, pastes and granules.

These formulations may be produced in known manner, for example by mixing the active compounds with extenders, that is to say liquid or solid diluents or carriers, optionally with the use of surface-active agents, that is to say emulsifying agents and/or dispersing agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound combinations according to the invention can be present in the formulations as a mixture with other known active compounds, such as fungicides, insecticides, acaricides and herbicides, and also as mixtures with fertilizers.

The active compound combinations can be used as such, in the form of their formulations or as the use forms prepared therefrom, such as ready-to-use solutions, emulsifiable concentrates, emulsions, suspensions, wettable powders, soluble powders and granules. They may be used in the customary manner, for example by watering, spraying, atomising, scattering and the like.

The active compound concentrations can be varied within a substantial range. In general, 0.01 to 50 kg, preferably 0.05 to 10 kg, of the active compound are employed per hectare of soil surface.

The preferred time of application of the growth regulators depends on the climatic and vegetative circumstances.

Thus, the invention also provides a method of inhibiting the growth of cereals which comprises applying to the cereals, or to a habitat thereof, a composition according to the present invention.

The invention also provides cereals, the growth of which has been inhibited by a method according to the present invention.

The good growth-inhibiting action of the active compound combinations according to the invention on cereals can be seen from the examples which follow. While the individual active compounds have weaknesses in growth-inhibiting action, the combinations show an action which goes beyond a simple additive action.

A synergistic effect exists with growth inhibitors whenever the growth-inhibiting action of the active compound combination is greater than that of the individually applied active compounds.

The action to be expected for a given combination of two growth inhibitors can be calculated as follows (see Colby, S. R., "Calculating synergistic and antagonistic responses of herbicide combinations," Weeds 15, pages 20–22, 1967):

If $X = \%$ inhibition of growth by active compound A used in an amount of p kg/ha and $Y = \%$ inhibition of growth by active compound B used in an amount of q kg/ha and $E = $ the expected inhibition of growth by active compounds A and B used in amounts of p and q kg/ha then $$E = X + Y - (X \cdot Y/100)$$

If the actual inhibition of growth is greater than calculated, the action of the combination is superadditive, that is to say a synergistic effect exists.

The tables in Examples A and B show clearly that the found growth-inhibiting action of the active compound combinations according to the invention on cereals is greater than the calculated action, that is to say a true synergistic effect exists.

The active compounds indicated below were employed in the tests in the Examples which follow:

(I-1) = Cl—CH$_2$—CH$_2$—SO$_2$—CH$_2$—OH 2-chloroethyl hydroxymethyl sulphone (II-1) = Cl—CH$_2$—CH$_2$—N$^\oplus$(CH$_3$)$_3$ Cl$^\ominus$ (2-chloroethyl)-trimethyl-ammonium chloride In the Examples which follow, the "found" values of the inhibition of growth are those determined experimentally, whilst the "calculated" values are those derived by means of S. R. Colby's formula, referred to above.

EXAMPLE A

Inhibition of growth of winter barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up with water to the desired concentration. In the case of active compound combinations, the second active compound was dissolved in the same manner and the solution was added to the solution of the first active compound in the desired ratio. The mixture was made up with water to the desired dilution.

Winter barley of the Vogelsanger Gold variety was grown in the open in the customary manner. When the last leaf appeared, the plants were sprayed with the active compound preparations using a spraying apparatus with fan jet nozzles. The amount of water used was 600 l/ha.

When the vegetative growth had ended, the growth height in the individual plots was measured and was calculated in % of the growth height of the untreated controls. 100% meant that growth had stopped and 0% denoted a growth corresponding to that of the control plants.

The active compounds, amounts used and results can be seen from the table which follows.

TABLE A

| Active compound or active compound combination | Amount used kg/ha | Inhibition of growth in % found | Inhibition of growth in % calculated |
|---|---|---|---|
| (I-1) (known) | 2 | 5 | |
| | 4 | 12 | |
| (II-1) (known) | 0.35 | 1 | |
| | 0.7 | 2 | |
| (I-1) + (II-1) (according to the invention) | 2 + 0.35 | 8 | 5.95 |
| | 4 + 0.35 | 14 | 12.9 |
| | 2 + 0.7 | 10 | 6.9 |
| | 4 + 0.7 | 15 | 13.76 |

EXAMPLE B

Inhibition of growth of winter wheat

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up with water to the desired concentration. In the case of active compound combinations, the second active compound was dissolved in the same manner and the solution was added to the solution of the first active compound in the desired ratio. The mixture was made up with water to the desired dilution.

Winter wheat of the Kranich variety was grown in the open in the customary manner. At various times in the development of the cereal, the active compound preparations were applied to the plants using a spraying apparatus with fan jet nozzles. The amount of water used was 600 l/ha. When the vegetative growth had ended, the growth height of the cereal in the plots was measured and compared with the growth height of the untreated controls. 100% meant that growth had stopped and 0% denoted a growth corresponding to that of the control plants.

The active compounds, amounts used, stages of development of the plants and results can be seen from the table which follows.

TABLE B

| Active compound or active compound combination | Amount used kg/ha | Stage of the plants when treated | Inhibition of growth in % found | Inhibition of growth in % calculated |
|---|---|---|---|---|
| (I-1) | 2 | 1st node stage | 1 | |
| (II-1) (known) | 0.7 | 1st node stage | 20 | |
| (I-1) + (II-1) (according to the invention) | 2 + 0.7 | 1st node stage | 25 | 20.8 |
| (I-1) (known) | 4 | 2nd node stage | 1 | |
| (II-1) (known) | 0.7 | 2nd node stage | 19 | |
| (I-1) + | 4 + 0.7 | 2nd node | 27 | 19.8 |

TABLE B-continued

Inhibition of growth of winter wheat

| Active compound or active compound combination | Amount used kg/ha | Stage of the plants when treated | Inhibition of growth in % | |
|---|---|---|---|---|
| | | | found | calculated |
| (II-1) (according to the invention) | | stage | | |

It will be understood that the specification and examples are illustrative, but not limitative, of the present invention and that other embodiments within the spirit and scope of the invention will suggest themselves to those skilled in the art.

What is claimed is:

1. Composition for inhibiting the growth of cereals comprising, as active ingredients,
   (a) one haloethylsulfone of the formula

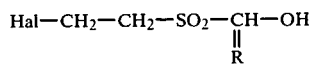   (I)

wherein
   Hal is halogen and
   R is hydrogen or alkyl of 1 to 6 carbon atoms and
   (b) one (2-chloroethyl)-trimethylammonium compound of the Formula

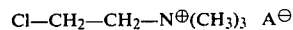   (II)

wherein
   $A^{\ominus}$ is a halide, tetrafluoroborate or alkylsulphate, and the proportion of ingredient (a) to ingredient (b) is from 1:0.04 to 1:2.

2. Composition as claimed in claim 1 also comprising an inert carrier in admixture with said active ingredients.

3. Composition as claimed in claim 1 wherein in the compound of formula (I), Hal is chlorine or bromine and R is alkyl of from 1 to 4 carbon atoms.

4. Composition as claimed in claim 1 wherein said weight ratio is from 1:0.07 to 1:0.5.

5. Composition as claimed in claim 1 wherein said composition contains 0.1 to 95% by weight of total active compound.

6. Method for inhibiting the growth of cereals which method comprises applying to the cereals or their habitat a composition as claimed in claim 1.

7. Method as claimed in claim 6 wherein an amount of 0.01 to 50 kg of said composition is applied per hectare.

8. Method as claimed in claim 6 wherein an amount of 0.05 to 10 kg of said composition is applied per hectare.

9. Method as claimed in claim 6 wherein said cereal is wheat.

10. Method as claimed in claim 6 wherein said cereal is oats.

11. Method as claimed in claim 6 wherein said cereal is rye.

12. Method as claimed in claim 6 wherein said cereal is barley.

13. Method as claimed in claim 6 wherein said cereal is rice.

14. Method as claimed in claim 6 wherein the weight ratio of said component (a) to said component (b) is from 1:0.07 to 1:05.

15. Method as claimed in claim 6 wherein component (a) is 2-chloroethyl hydroxymethyl sulfone and component (b) is (2-chloroethyl)-trimethyl-ammonium chloride.

* * * * *